United States Patent
Steel et al.

(10) Patent No.: US 10,195,346 B2
(45) Date of Patent: Feb. 5, 2019

(54) DRUG DELIVERY DEVICE

(71) Applicant: SANOFI-AVENTIS DEUTSCHLAND GMBH, Frankurt am Main (DE)

(72) Inventors: Samuel Steel, Warwickshire (GB); Paul Richard Draper, Warwickshire (GB); Joseph Butler, Warwickshire (GB); George Cave, Warwickshire (GB); David Richard Mercer, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 369 days.

(21) Appl. No.: 14/763,864

(22) PCT Filed: Jan. 27, 2014

(86) PCT No.: PCT/EP2014/051469
§ 371 (c)(1),
(2) Date: Jul. 28, 2015

(87) PCT Pub. No.: WO2014/118106
PCT Pub. Date: Aug. 7, 2014

(65) Prior Publication Data
US 2015/0359967 A1 Dec. 17, 2015

(30) Foreign Application Priority Data
Jan. 29, 2013 (EP) .................................... 13153136

(51) Int. Cl.
*A61M 5/30* (2006.01)
*A61M 5/31* (2006.01)
(Continued)

(52) U.S. Cl.
CPC ............... *A61M 5/31* (2013.01); *A61M 5/20* (2013.01); *A61M 5/24* (2013.01);
(Continued)

(58) Field of Classification Search
CPC ................................................. A61M 2205/14
See application file for complete search history.

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 101340938 A | 1/2009 |
| CN | 102740907 A | 10/2012 |

(Continued)

OTHER PUBLICATIONS

European Search Report for EP App. No. 13153136.0, dated May 6, 2013.

(Continued)

*Primary Examiner* — Andrew Gilbert
(74) *Attorney, Agent, or Firm* — Fish & Richardson P.C.

(57) ABSTRACT

A drug delivery device for administering a drug is presented having a body adapted to retain a cartridge containing a drug, at least one electrical unit and a port for electrically contacting the electrical unit, an adapter for attaching an injection needle to the drug delivery device, a safety mechanism arranged to prevent contacting the electrical unit through the port whilst an injection needle is in fluid communication with the cartridge and arranged to prevent establishing a fluid communication between an injection needle and the cartridge whilst the port is configured to allow contacting the electrical unit.

11 Claims, 5 Drawing Sheets

(51) Int. Cl.
*A61M 5/20* (2006.01)
*A61M 5/24* (2006.01)
*A61M 5/34* (2006.01)
*A61M 5/315* (2006.01)
*A61M 5/32* (2006.01)

(52) U.S. Cl.
CPC ...... *A61M 5/31566* (2013.01); *A61M 5/3202* (2013.01); *A61M 5/34* (2013.01); *A61M 5/345* (2013.01); *A61M 5/347* (2013.01); *A61M 2005/206* (2013.01); *A61M 2205/50* (2013.01); *A61M 2205/502* (2013.01); *A61M 2205/8237* (2013.01); *A61M 2205/8262* (2013.01)

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Harber et al. | |
| 5,383,865 A | 1/1995 | Michel | |
| 5,401,251 A * | 3/1995 | Hui | A61M 5/3216 604/192 |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,691,495 A | 11/1997 | Fujimori | |
| 5,921,966 A | 7/1999 | Bendek et al. | |
| 6,004,297 A | 12/1999 | Steenfeldt-Jensen et al. | |
| 6,171,276 B1 * | 1/2001 | Lippe | A61M 5/20 128/DIG. 1 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,704,231 B2 * | 4/2010 | Pongpairochana | A61M 5/20 604/131 |
| 8,206,351 B2 * | 6/2012 | Sugimoto | A61M 5/20 604/151 |
| 9,339,605 B2 * | 5/2016 | Wimpenny | A61M 5/002 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2009/0275916 A1 | 11/2009 | Harms et al. | |
| 2012/0130346 A1 * | 5/2012 | Davies | A61M 5/2448 604/506 |
| 2013/0079708 A1 * | 3/2013 | Wimpenny | A61M 5/002 604/65 |
| 2013/0245604 A1 * | 9/2013 | Kouyoumjian | A61M 5/1408 604/506 |
| 2013/0310756 A1 * | 11/2013 | Whalley | A61M 5/31 604/189 |
| 2014/0142507 A1 * | 5/2014 | Armes | A61M 5/422 604/112 |
| 2015/0182706 A1 * | 7/2015 | Wurmbauer | A61M 5/34 604/111 |
| 2015/0320932 A1 * | 11/2015 | Draper | A61M 5/20 604/131 |
| 2015/0367074 A1 * | 12/2015 | Draper | A61M 5/20 604/198 |
| 2015/0367075 A1 * | 12/2015 | Cave | A61M 5/20 604/241 |
| 2016/0296700 A1 * | 10/2016 | Kikuchi | A61M 5/36 |

FOREIGN PATENT DOCUMENTS

| | | |
|---|---|---|
| EP | 0937471 | 8/1999 |
| EP | 0937476 | 8/1999 |
| EP | 0938554 | 8/1999 |
| WO | WO 97/48803 | 12/1997 |
| WO | WO 01/10484 | 2/2001 |
| WO | 2008/045203 | 4/2008 |
| WO | 2009/113060 | 9/2009 |
| WO | 2011/117404 | 9/2011 |
| WO | WO2011117404 A2 * | 9/2011 |

OTHER PUBLICATIONS

International Search Report and Written Opinion for Int. App. No. PCT/EP2014/051469, dated Feb. 27, 2014.
English translation of 1st Office Action and Search Report for corresponding Chinese patent application No. CN 201480005968.1, dated May 27, 2017.
English translation of 2nd Office Action and Search Report for corresponding Chinese patent application No. CN 201480005968.1, dated Dec. 21, 2017.
English translation of 1st Office Action for corresponding Japanese patent application No. JP 2015-554166, dated Oct. 17, 2017.
International Preliminary Report on Patentability issued in International Application No. PCT/EP2014/051469, dated Aug. 4, 2015, 7 pages.

* cited by examiner

DRUG DELIVERY DEVICE

CROSS REFERENCE TO RELATED APPLICATIONS

The present application is a U.S. National Phase Application pursuant to 35 U.S.C. § 371 of International Application No. PCT/EP2014/051469 filed Jan. 27, 2014, which claims priority to European Patent Application No. 13153136.0 filed Jan. 29, 2013. The entire disclosure contents of these applications are herewith incorporated by reference into the present application.

TECHNICAL FIELD

The invention relates to a drug delivery device.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring. In other devices this is achieved by an electromechanical drive. Devices with electromechanical and/or electronic components may comprise a port which may serve for wired communication with another device for data transfer or for charging.

SUMMARY

It is an object of the present invention to provide an improved drug delivery device.

The object is achieved by a drug delivery device according to claim 1.

Preferred embodiments of the invention are given in the dependent claims.

According to the invention a drug delivery device for administering a drug, comprises:
  a body adapted to retain a cartridge containing a drug,
  at least one electrical unit and a port for electrically contacting the electrical unit,
  an adapter for attaching an injection needle to the drug delivery device,
  a safety mechanism arranged to prevent contacting the electrical unit through the port whilst an injection needle is in fluid communication with the cartridge and arranged to prevent establishing a fluid communication between an injection needle and the cartridge whilst the port is configured to allow contacting the electrical unit.

The port, e.g. a USB port, may serve for wired communication with another device for data transfer or charging. The safety mechanism avoids the risk that the user may inadvertently leave the drug delivery device connected via a cable whilst attempting to inject. In this case there may exist a potential conductive path from the externally connected device, through the cable, the port and the electronics of the drug delivery device to the patient via the conductive metal injection needle. In case of a current overload on the port or a leaking cartridge which creates a short-circuit within the drug delivery device, the patient would be subjected to an electric shock. An electric shock may occur either if both the patient and the external device connected to the port are grounded or if the patient touches the port whilst they were injecting regardless of whether a cable is connected to the port or not. Similarly, the port may be adapted to interface with a blood glucose strip for measuring a user's blood glucose value. The port will thus also feature electronic contacts. Consequently there is a similar associated risk. The safety mechanism according to the invention prevents this risk.

The above risk is addressed by providing a safety mechanism arranged to prevent access to the port whilst an injection needle is in fluid communication with the cartridge and arranged to prevent establishing a fluid communication between an injection needle and the cartridge whilst the port is accessible.

Other options would be to have the safety mechanism disable the dosing operation of the drug delivery device when the user can access the port. This may be achieved by performing an operation which disables a delivery mechanism of the drug delivery device or by preventing the user from accessing a button or soft button on a human-machine interface for operating the drug delivery device.

In an exemplary embodiment the adapter comprises a threaded area for mounting a threaded needle. Instead of the threaded area the adapter may comprise other means for attaching the needle such as a bayonet fit, a cone or a Luer-lock.

The port may be arranged within the body behind an opening in the body.

In an exemplary embodiment a movable cover is arranged for exposing the opening in an open position or obscuring the opening in a closed position.

The cover may be slidably and/or rotatably arranged with respect to the body.

A spring may be arranged for biasing the cover towards the open position.

In another exemplary embodiment a handle may be arranged on the cover for facilitating operation.

In an exemplary embodiment a distal end of the cover protrudes into the range of the adapter in such a manner that the distal end interferes with a needle hub of the needle being assembled to the adapter such that the needle hub displaces the distal end and the cover towards the closed position thus ensuring that the cover cannot expose the port when a needle is assembled to the adapter.

In an exemplary embodiment the cover comprises a sleeve shaped distal end, which in the open position protrudes in the distal direction to such an extent that an attached needle is hidden within the sleeve shaped distal end preventing its insertion into an injection site, wherein in the closed position the sleeve shaped distal end is retracted to at least partially expose the needle.

In an exemplary embodiment the cover is arranged as part of a needle collar telescoped with the body, wherein when the needle is assembled to the needle collar and the needle cover is in the open position, a proximal tip of the needle is spaced from a septum of the cartridge, wherein the proximal tip of the needle pierces the septum when the needle collar with the assembled needle is moved into the closed position. Although this embodiment allows for mounting a needle while the port is accessible the needle cannot establish a fluid communication thus mitigating the aforesaid risks.

In an exemplary embodiment the needle collar has a thread interface with the body such that the needle collar has to be rotated in order to move between the open and the closed position. If the adapter also comprises a thread for assembling a threaded needle the user just screws the needle onto the adapter and keeps on rotating thereby displacing the needle collar towards the closed position while the needle pierces the septum.

In an exemplary embodiment a pitch of the thread interface between the needle collar and the body is greater than or equal to a length of the port or the opening in a longitudinal direction to ensure less than one revolution of the needle collar around the body will result in an axial travel equal to the length of the port.

In an exemplary embodiment the port is housed within an opening in the adapter such that when a needle is attached to the adapter a needle hub of the needle covers the opening and thus the port. This embodiment is particularly simple and cost-efficient as it avoids further movable part.

In an exemplary embodiment the port is arranged on a communication port subassembly comprising a port hub attachable to the adapter, wherein the port hub comprises at least two electrical contacts connected to the communication port and arranged to contact a respective number of electrical contacts on or adjacent the adapter when the communication port subassembly is attached to the adapter.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
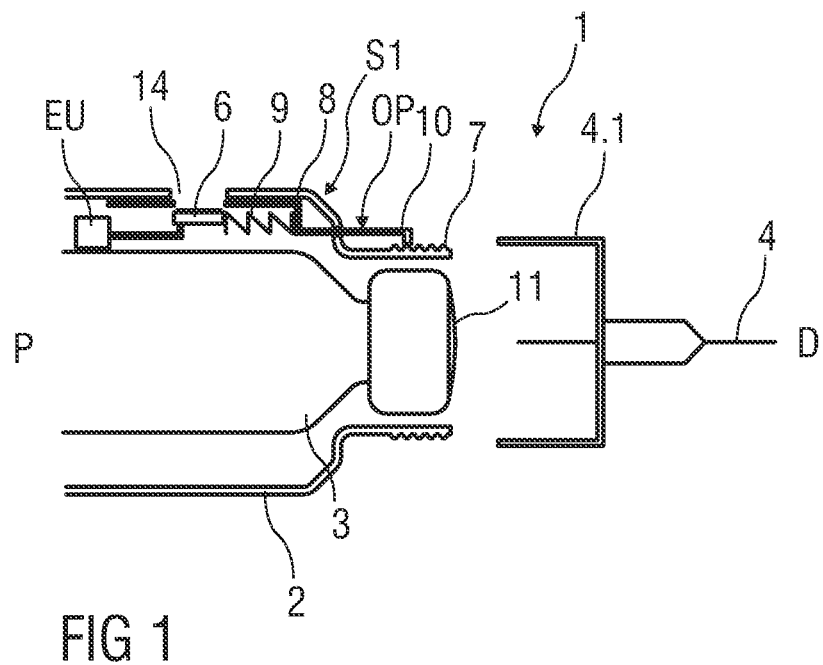
FIG. 1 is a schematic longitudinal section of a first exemplary embodiment of an electromechanical drug delivery device for administering a drug comprising a port and a sliding cover in an open position.

FIG. 1 is a schematic longitudinal section of a first exemplary embodiment of an electromechanical drug delivery device 1 for administering a drug. The drug delivery device 1 comprises a body 2 adapted to receive a drug cartridge 3 or syringe. A hypodermic needle 4 may be attached to the cartridge 3, preferably a needle 4 with two tips, one of them for piercing an injection site and the other for piercing a septum 11 on the cartridge 3 for establishing a fluid communication between the cartridge 3 and the needle 4. The drug delivery device 1 further comprises at least one electric unit EU or electronic device such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The body 2 comprises an adapter 7 for attaching the needle 4. The adapter 7 may be arranged as a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging. There is an associated risk with this feature that the user may inadvertently leave the drug delivery device 1 connected via a cable whilst attempting to inject. Whilst a control unit of the drug delivery device 1 may run software including checks to prevent the delivery of the drug in this situation, there will still exist a potential conductive path from the externally connected device, through the cable, the port 6 and the electronics of the drug delivery device 1 to the patient via the conductive metal needle 4. It is thus possible that, for instance, a current overload on the port 6 or a leaking cartridge 3 which creates a short-circuit within the drug delivery device 1, could deliver an electric shock to the patient. This may occur either if both the patient and the external device connected to the port 6 are grounded or if the patient touches the port 6 whilst they were injecting regardless of whether a cable is connected to the port 6 or not.

Similarly, the port 6 may be adapted to interface with a blood glucose strip for measuring a user's blood glucose value. The port 6 will thus also feature electronic contacts. Consequently there is a similar associated risk.

The above risk is addressed by providing a safety mechanism to disable the dosing operation of the drug delivery device 1 when the user can access the port 6. This is achieved by performing an operation which disables a delivery mechanism of the drug delivery device 1 or by preventing the user from accessing an adapter 7 such as a threaded area 7 of the drug delivery device 1 adapted to connect to the needle 4 or from accessing a button or soft button on the human-machine interface.

Figure 2:
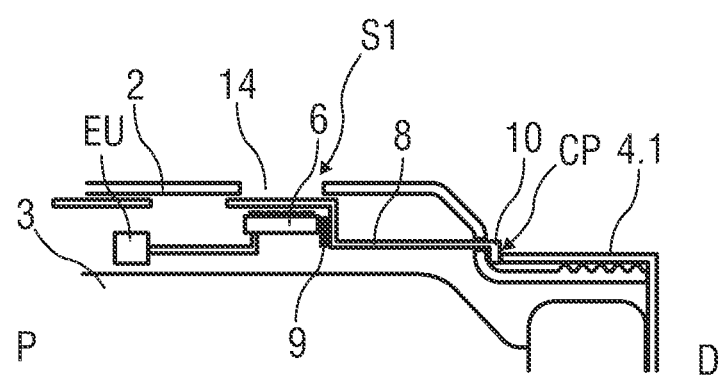
FIG. 2 is a schematic longitudinal detail section of the a first embodiment of the electromechanical drug delivery device, wherein the sliding cover is in a closed position.

In the embodiment of FIG. 1 the port is housed within an opening 14 within the body 2. The adapter 7 or threaded area 7 of the drug delivery device 1 is arranged on the body 2. The safety mechanism S1 comprises a sliding cover 8 arranged slidably relative to the body 2 between a distal open position OP as illustrated in FIG. 1 and a proximal closed position CP as illustrated in FIG. 2, where the cover 8 obscures the opening 14 and the port 6. A spring 9 is arranged to bias the cover 8 towards the distal open position OP, in which the cover 8 is removed from the opening 14 so as to expose the port 6. A distal end 10 of the cover 8 protrudes through the body 2 in a distal direction D into the range of the adapter 7 in such a manner that the distal end 10 interferes with a needle hub 4.1 of the needle 4 during assembly of the needle 4. If a needle 4 is assembled, e.g. screwed onto the adapter 7, the needle hub 4.1 displaces the distal end 10 and thus the cover 8 towards the proximal closed position CP against the bias of the spring 9 as illustrated in FIG. 2, such that the port 6 is inaccessible when a needle 4 is attached. When no needle 4 is present the spring 9 is allowed to relax and move the cover 8 towards the distal open position OP thus exposing the port 6 and allowing access.

Figure 3:
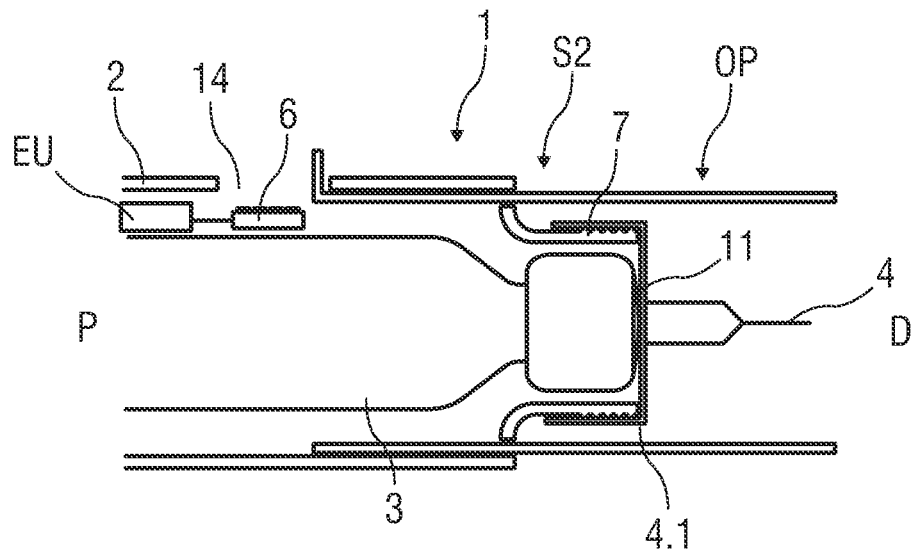
FIG. 3 is a longitudinal section of a second exemplary embodiment of the drug delivery device with a sleeve shaped needle guard.

FIG. 3 is a longitudinal section of a second exemplary embodiment of the drug delivery device 1.

The drug delivery device 1 comprises a body 2 adapted to receive a drug cartridge 3 or syringe. A hypodermic needle 4 may be attached to the cartridge 3, preferably a needle 4 with two tips, one of them for piercing an injection site and the other for piercing a septum 11 on the cartridge 3 for establishing a fluid communication between the cartridge 3 and the needle 4. The drug delivery device 1 further comprises at least one electrical unit EU such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The body 2 comprises an adapter 7 for attaching the needle 4. The adapter 7 may be arranged as a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging.

In the embodiment of FIG. 3 the port is housed within an opening 14 within the body 2. The adapter 7 or threaded area 7 of the drug delivery device 1 is arranged on the body 2. The safety mechanism S2 comprises a sliding cover 8 arranged slidably relative to the body 2 between a distal open position OP as illustrated in FIG. 3 and a proximal closed position CP (not illustrated), where the cover 8 obscures the opening 14 and the port 6. A spring (not illustrated) may be arranged to bias the cover 8 towards the distal open position OP, in which the cover 8 is removed from the opening 14 so as to expose the port 6. A distal end 10 of the cover 8 protrudes through the body 2 in a distal direction D and takes the shape of a sleeve needle guard. As the sliding cover 8 is in the distal open position OP the needle guard 10 protrudes in the distal direction D to such an extent that the needle 4 is hidden within needle guard 10 and cannot be inserted into an injection site such as a patient's skin. If the needle guard 10 is moved in a proximal direction P the cover 8 is moved towards its proximal closed position CP obscuring the port 6 while the needle 4 is exposed for allowing insertion into an injection site. Other than in the embodiment of FIGS. 1 and 2 the port 6 may be accessible when a needle 4 is attached. However, as the port 6 is accessible the needle 4 cannot be inserted thus also mitigating the above described risk.

Figure 4:
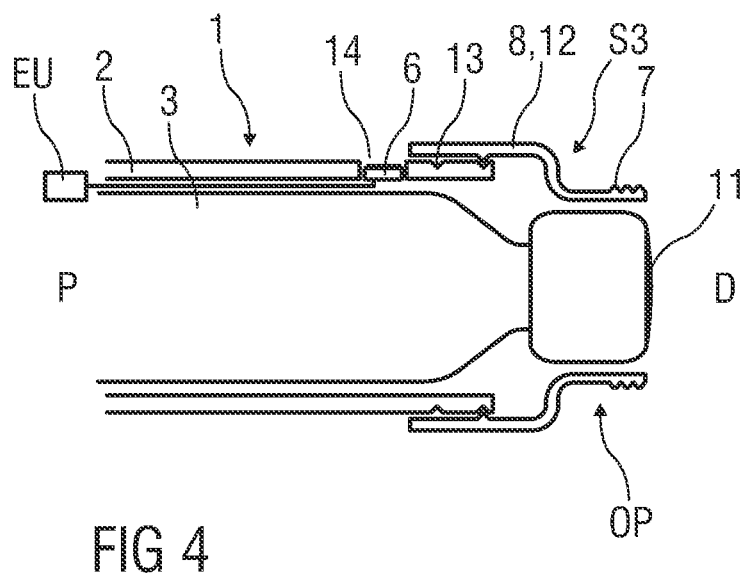
FIG. 4 is a longitudinal section of a third exemplary embodiment of the drug delivery device with a needle collar in an open position.

FIG. 4 is a longitudinal section of a third exemplary embodiment of the drug delivery device 1.

The drug delivery device 1 comprises a body 2 adapted to receive a drug cartridge 3 or syringe. A hypodermic needle 4 (cf. FIG. 5) may be attached to the cartridge 3, preferably a needle 4 with two tips, one of them for piercing an injection site and the other for piercing a septum 11 on the cartridge 3 for establishing a fluid communication between the cartridge 3 and the needle 4. The drug delivery device 1 further comprises at least one electrical unit EU such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The drug delivery device 1 comprises an adapter 7 for attaching the needle 4. The adapter 7 may be arranged as a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging.

In the embodiment of FIG. 4 the port is housed within an opening 14 in the body 2. The safety mechanism S3 comprises a cover 8 arranged as part of a needle collar 12 telescoped with the body 2.

The needle collar 12 has a thread interface 13 with the body 2 whose pitch may be greater than or equal to a length of the port 6 or the opening 14 in a longitudinal direction D, P; to ensure less than one revolution of the needle collar around the body 2 will result in an axial travel equal to the length of the port. The adapter 7 is also arranged on the needle collar 12 to allow the needle 4 to assemble to the drug delivery device 1. The adapter 7 is preferably threaded to allow assembly of a threaded needle 4.

When a needle 4 is not assembled to the drug delivery device 1 the needle collar 12 is in its distal open position OP, shown in FIG. 4. In this state the port 6, located in the opening 14 in the body 2, is accessible to the user.

Figure 5:
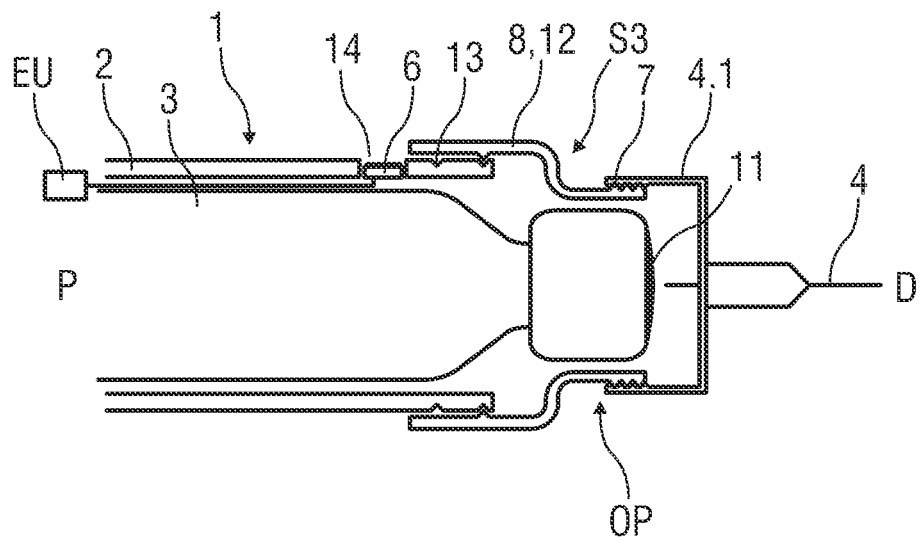
FIG. 5 is a longitudinal section of the third embodiment of the drug delivery device with the needle collar in the open position and a needle attached to the needle collar.

The needle 4 assembles to the needle collar 12 using the thread interface of the adapter 7. When the needle 4 is fully assembled to the needle collar 12, the port 6 is still accessible to the user; however the proximal tip of the needle 4 has not yet pierced the septum 11. FIG. 5 is a longitudinal section of the third exemplary embodiment of the drug delivery device 1 with the needle 4 assembled to the adapter 7 on the needle collar 12.

Figure 6:
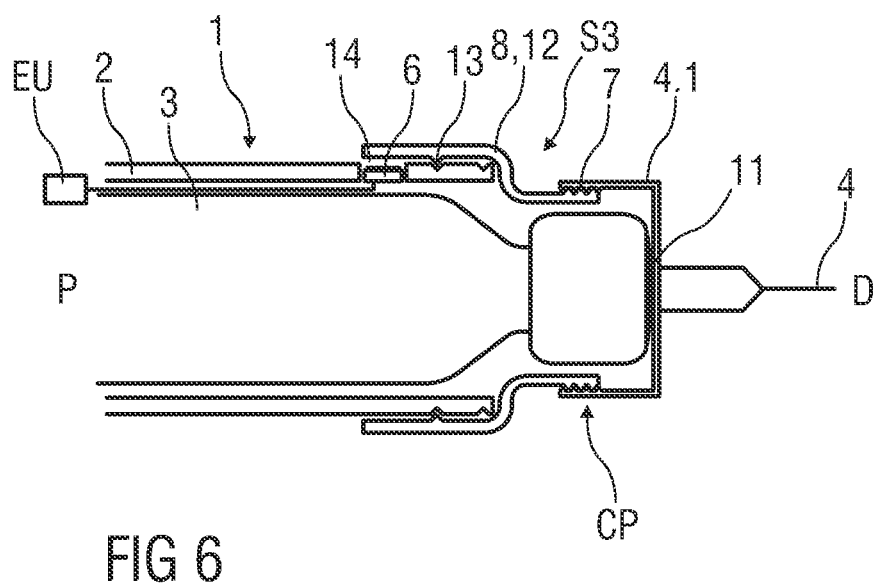
FIG. 6 is a longitudinal section of the third embodiment of the drug delivery device with the needle collar in a closed position and the needle attached to the needle collar.

After the needle 4 is fully assembled to the needle collar 12, the user continues to apply torque to the needle 4. This forces the needle 4 and the needle collar 12 to take the helical path provided by the thread interface 13 between the needle collar and the body 2. The needle 4 thus moves towards the cartridge 3 and the proximal tip of the needle 4 pierces the septum while the needle collar 12 moves over the opening 14 thus obscuring the port 6. FIG. 6 is a longitudinal section of the third exemplary embodiment of the drug delivery device 1 with the needle 4 assembled to the adapter 7 on the needle collar 12 and the needle collar 12 obscuring the port 6.

Figure 7:
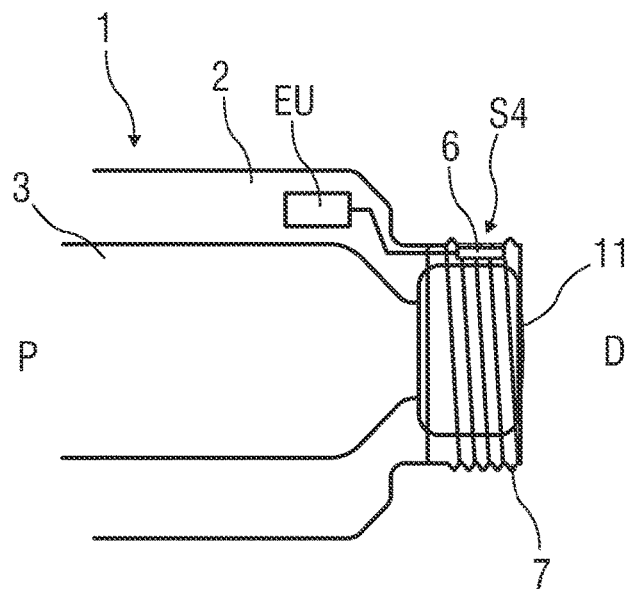
FIG. 7 is a longitudinal section of a fourth exemplary embodiment of the drug delivery device with the port housed in an opening within an adapter for mounting a needle.

FIG. 7 is a longitudinal section of a fourth exemplary embodiment of the drug delivery device 1.

The drug delivery device 1 comprises a body 2 adapted to receive a drug cartridge 3 or syringe. A hypodermic needle 4, not illustrated but similar to the needles 4 in the previously described embodiments, may be attached to the cartridge 3, preferably a needle 4 with two tips, one of them for piercing an injection site and the other for piercing a septum 11 on the cartridge 3 for establishing a fluid communication between the cartridge 3 and the needle 4. The drug delivery device 1 further comprises at least one electrical unit EU such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The body 2 comprises an adapter 7 for attaching the needle 4. The adapter 7 may be arranged as a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging.

In the embodiment of FIG. 7 the safety mechanism S4 is provided by housing the port 6 within an opening 14 in the adapter 7. The port 6 is accessible if no needle 4 is attached to the adapter 7. When a needle 4 is attached the needle hub 4.1 covers the opening 14 and thus the port 6, making it non-accessible.

Figure 8:
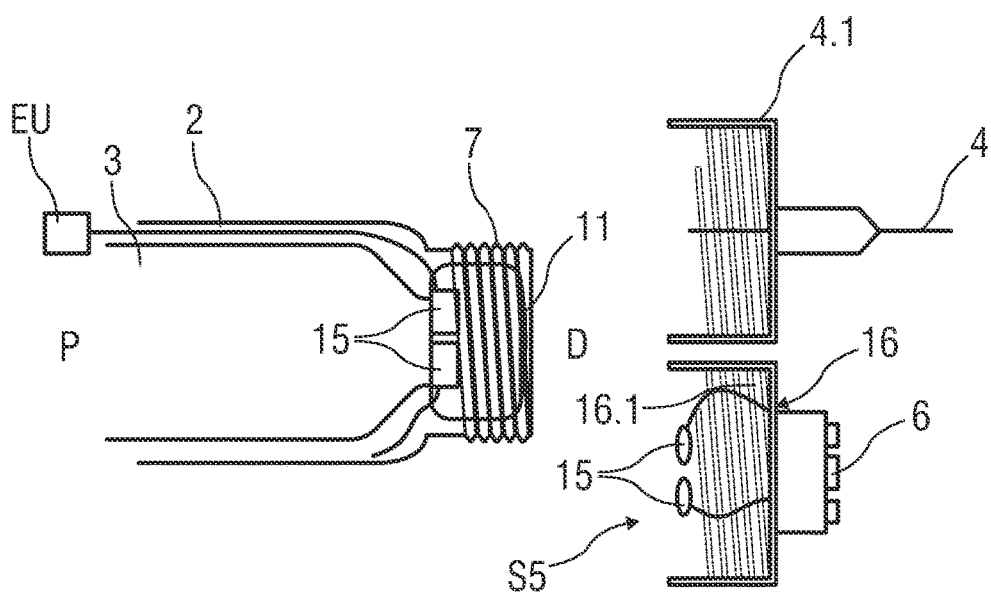
FIG. 8 is a longitudinal section of a fourth exemplary embodiment of the drug delivery device, wherein the port is arranged on a communication port subassembly which may be mounted to the adapter.

FIG. 8 is a longitudinal section of a fifth exemplary embodiment of the drug delivery device 1.

The drug delivery device 1 comprises a body 2 adapted to receive a drug cartridge 3 or syringe. A hypodermic needle 4 may be attached to the cartridge 3, preferably a needle 4 with two tips, one of them for piercing an injection site and the other for piercing a septum 11 on the cartridge 3 for establishing a fluid communication between the cartridge 3 and the needle 4. The drug delivery device 1 further comprises at least one electrical unit EU such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The body 2 comprises an adapter 7 for attaching the needle 4. The adapter 7 may be arranged as or comprise a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging. The safety mechanism S5 is provided by the port 6 being arranged on a communication port subassembly 16 comprising a port hub 16.1 similar to the needle hub 4.1. The port hub 16.1 comprises a thread interface similar to the one of the needle hub 4.1 such that either the needle 4 or the communication port subassembly 16 may be attached to the adapter 7. Furthermore the port hub 16.1 comprises at least two electrical contacts 15 connected to the communication port 6 and arranged to contact a respective number of electrical contacts on or adjacent the adapter 7 when the communication port subassembly 16 is completely screwed onto the adapter 7.

The port 6 can therefore only be attached to the drug delivery device if no needle 4 is present. On the other hand, attaching a needle 4 requires that the communication port subassembly 16 is not attached.

Figure 9:
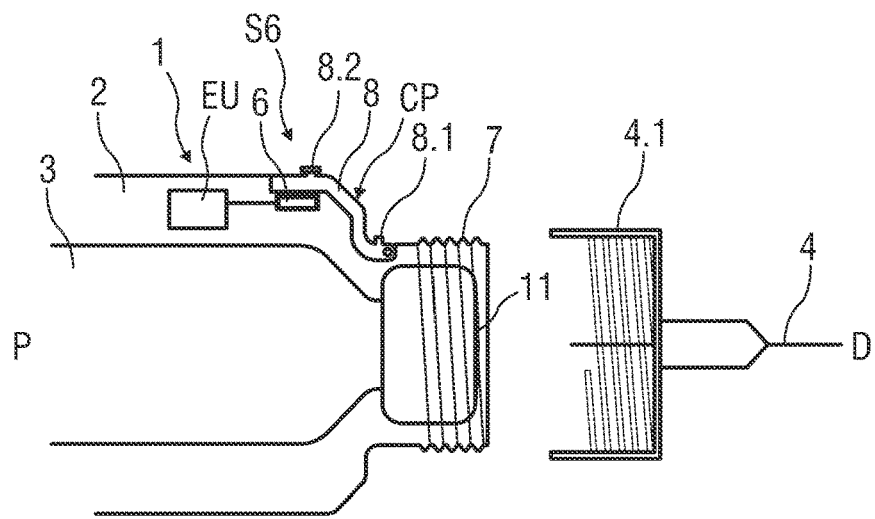
FIG. 9 is a schematic longitudinal section of a sixth exemplary embodiment of the electromechanical drug delivery device comprising a port and a rotatable cover in a closed position.

FIG. 9 is a schematic longitudinal section of a sixth exemplary embodiment of an electromechanical drug delivery device 1 for administering a drug. The drug delivery device 1 comprises a body 2 adapted to receive a drug cartridge 3 or syringe. A hypodermic needle 4 may be attached to the cartridge 3, preferably a needle 4 with two tips, one of them for piercing an injection site and the other for piercing a septum 11 on the cartridge 3 for establishing a fluid communication between the cartridge 3 and the needle 4. The drug delivery device 1 further comprises at least one electrical unit EU such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The body 2 comprises an adapter 7 for attaching the needle 4. The adapter 7 may be arranged as a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging.

Figure 10:
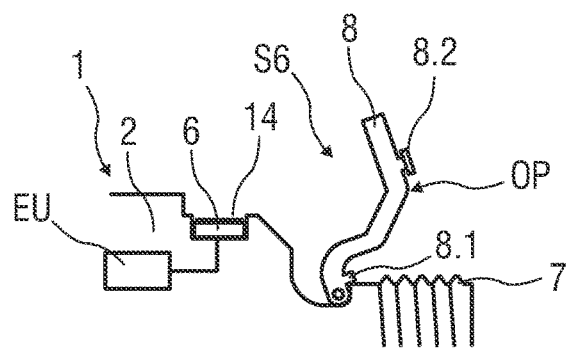
FIG. 10 is a schematic longitudinal section of the sixth embodiment of the electromechanical drug delivery device with the cover in an open position.
Figure 11:
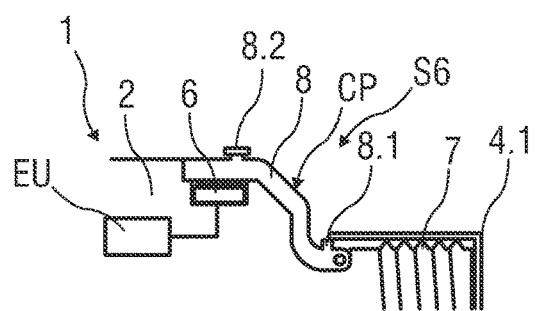
FIG. 11 is a schematic longitudinal section of the sixth embodiment of the electromechanical drug delivery device with a needle attached displacing the cover into the closed position.

In the embodiment of FIG. 9 the port is housed within an opening 14 within the body 2. The adapter 7 or threaded area 7 of the drug delivery device 1 is arranged on the body 2. The safety mechanism S6 comprises a folding cover 8 pivoted on the body 2 between a closed position CP as illustrated in FIG. 9 and an open position OP as illustrated in FIG. 10, where the cover 8 exposes the opening 14 and the port 6. A spring (not illustrated) may be arranged to bias the cover 8 towards the open position OP, in which the cover 8 is removed from the opening 14 so as to expose the port 6. An engagement surface 8.1 such as a pin of the cover 8 is arranged adjacent the adapter 7 in such a manner that it interferes with a needle hub 4.1 of the needle 4 during assembly of the needle 4. If a needle 4 is assembled, e.g. screwed onto the adapter 7, the needle hub 4.1 displaces the engagement surface 8.1 and thus the cover 8 towards the closed position CP as illustrated in FIG. 11, such that the port 6 is inaccessible when a needle 4 is attached. When no needle 4 is present as in FIG. 10 the cover 8 may be rotated to the open position OP, e.g. by means of a handle 8.2 on the cover 8 or biased by a spring, thus exposing the port 6 and allowing access. Hence, as long as the needle 4 is attached, the cover 8 cannot be moved to the open position OP.

Instead of the threaded area 7 the adapter 7 may comprise other means for attaching the needle 4 such as a bayonet fit, a cone or a Luer-lock.

The safety mechanism may in general comprise either purely mechanical means or an electronically actuated mechanical system. The safety mechanism could potentially make use of physical detents or magnetic elements to assist in the latching of the parts into the open or closed positions.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38[ Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. Drug delivery device for administering a drug, comprising:
   a body adapted to retain a cartridge containing a drug,
   at least one electrical unit and a port for electrically contacting the at least one electrical unit,
   an adapter for attaching an injection needle to the drug delivery device,
   a safety mechanism arranged to prevent contacting the electrical unit through the port whilst an injection needle is in fluid communication with the cartridge and arranged to prevent establishing a fluid communication between an injection needle and the cartridge whilst the port is configured to allow contacting the electrical unit,
   wherein the port is arranged within the body behind an opening in the body,
   wherein a movable cover is arranged for exposing the opening in an open position or obscuring the opening in a closed position,
   wherein a distal end of the movable cover protrudes into a range of the adapter in such a manner that the distal end interferes with a needle hub of the injection needle being assembled to the adapter such that the needle hub displaces the distal end and the movable cover towards the closed position.

2. Drug delivery device according to claim 1, wherein the adapter comprises a threaded area for mounting a threaded needle.

3. Drug delivery device according to claim 1, wherein the movable cover is slidably arranged with respect to the body.

4. Drug delivery device according to claim 1, wherein the movable cover is rotatably arranged with respect to the body.

5. Drug delivery device according to claim 1, wherein a spring is arranged for biasing the movable cover towards the open position.

6. Drug delivery device according to claim 1, wherein a handle is arranged on the movable cover.

7. Drug delivery device for administering a drug, comprising:
   a body adapted to retain a cartridge containing a drug,
   at least one electrical unit and a port for electrically contacting the at least one electrical unit,
   an adapter for attaching an injection needle to the drug delivery device,
   a safety mechanism arranged to prevent contacting the at least one electrical unit through the port whilst the needle is inserted in an injection site and arranged to prevent insertion of the needle into an injection site whilst the port is configured to allow contacting the at least one electrical unit,
   wherein the port is arranged within the body behind an opening in the body,
   wherein a movable cover is arranged for exposing the opening in an open position or obscuring the opening in a closed position, wherein the movable cover comprises a sleeve shaped distal end, which in the open position protrudes in a distal direction to such an extent that an attached needle is hidden within the sleeve shaped distal end preventing its insertion into an injection site, wherein in the closed position the sleeve shaped distal end is retracted to at least partially expose the attached needle.

8. Drug delivery device for administering a drug, comprising:
   a body adapted to retain a cartridge containing a drug,
   at least one electrical unit and a port for electrically contacting the at least one electrical unit,
   an adapter for attaching an injection needle to the drug delivery device,
   a safety mechanism arranged to prevent contacting the electrical unit through the port whilst an injection needle is in fluid communication with the cartridge and arranged to prevent establishing a fluid communication between an injection needle and the cartridge whilst the port is configured to allow contacting the electrical unit,
   wherein the port is arranged within the body behind an opening in the body,
   wherein a movable cover is arranged for exposing the opening in an open position or obscuring the opening in a closed position, wherein the movable cover is arranged as part of a needle collar telescoped with the body, wherein when the injection needle is assembled to the needle collar and a needle cover is in the open position, a proximal tip of the needle is spaced from a septum of the cartridge, wherein the proximal tip of the injection needle pierces the septum when the needle collar with the assembled injection needle is moved into the closed position.

9. Drug delivery device according to claim 8, wherein the needle collar has a thread interface with the body.

10. Drug delivery device according to claim 9, wherein a pitch of the thread interface is greater than or equal to a length of the port or the opening in a longitudinal direction.

11. Drug delivery device for administering a drug, comprising:
    a body adapted to retain a cartridge containing a drug,
    at least one electrical unit and a port for electrically contacting the at least one electrical unit,
    an adapter for attaching an injection needle to the drug delivery device,
    a safety mechanism arranged to prevent contacting the electrical unit through the port whilst an injection needle is in fluid communication with the cartridge and arranged to prevent establishing a fluid communication between an injection needle and the cartridge whilst the port is configured to allow contacting the electrical unit, wherein the port is housed within an opening in the adapter such that when a needle is attached to the adapter a needle hub of the needle covers the opening and thus the port.

* * * * *